United States Patent [19]

Illy

[11] Patent Number: 4,708,485
[45] Date of Patent: Nov. 24, 1987

[54] APPARATUS FOR MONITORING A STREAM OF COMMINUTED SOLID MATERIAL

[75] Inventor: Ernesto Illy, Trieste, Italy

[73] Assignee: Illycaffé S.p.A., Trieste, Italy

[21] Appl. No.: 677,158

[22] Filed: Dec. 3, 1984

[30] Foreign Application Priority Data

Dec. 1, 1983 [IT] Italy .................. 23712/83[U]

[51] Int. Cl.$^4$ ................. G01N 21/01; G01N 21/17
[52] U.S. Cl. ................................ 356/440; 356/436
[58] Field of Search .................... 356/432–439, 356/335–338, 440; 250/573, 575–577, 574

[56] References Cited

U.S. PATENT DOCUMENTS

| | | | |
|---|---|---|---|
| 2,731,877 | 1/1956 | Clamann | 250/574 X |
| 3,834,818 | 9/1974 | Meric | 356/336 |
| 4,435,093 | 3/1984 | Krause et al. | 356/433 X |

FOREIGN PATENT DOCUMENTS

| | | | |
|---|---|---|---|
| 48766 | 5/1934 | Denmark | 356/439 |
| 3204456 | 8/1983 | Fed. Rep. of Germany | 356/432 |

*Primary Examiner*—Richard A. Rosenberger
*Attorney, Agent, or Firm*—Peter K. Kontler

[57] ABSTRACT

Apparatus for monitoring and analyzing a stream of powdered coal has an upright cylindrical vessel whose upper end receives the end portion of a conduit serving to deliver a stream of comminuted material in a gaseous carrier medium. The end portion of the conduit is coaxial with the vessel and is surrounded by a single annular nozzle or by an annulus of discrete nozzles serving to discharge first currents of compressed air into the vessel at a level above the discharge end of the conduit. The descending stream of comminuted material is traversed by several radial currents of compressed air close to the open lower end of the vessel and the thus treated stream of comminuted solid material descends into a second vessel wherein it is traversed and analyzed by a laser beam or a light beam.

11 Claims, 3 Drawing Figures

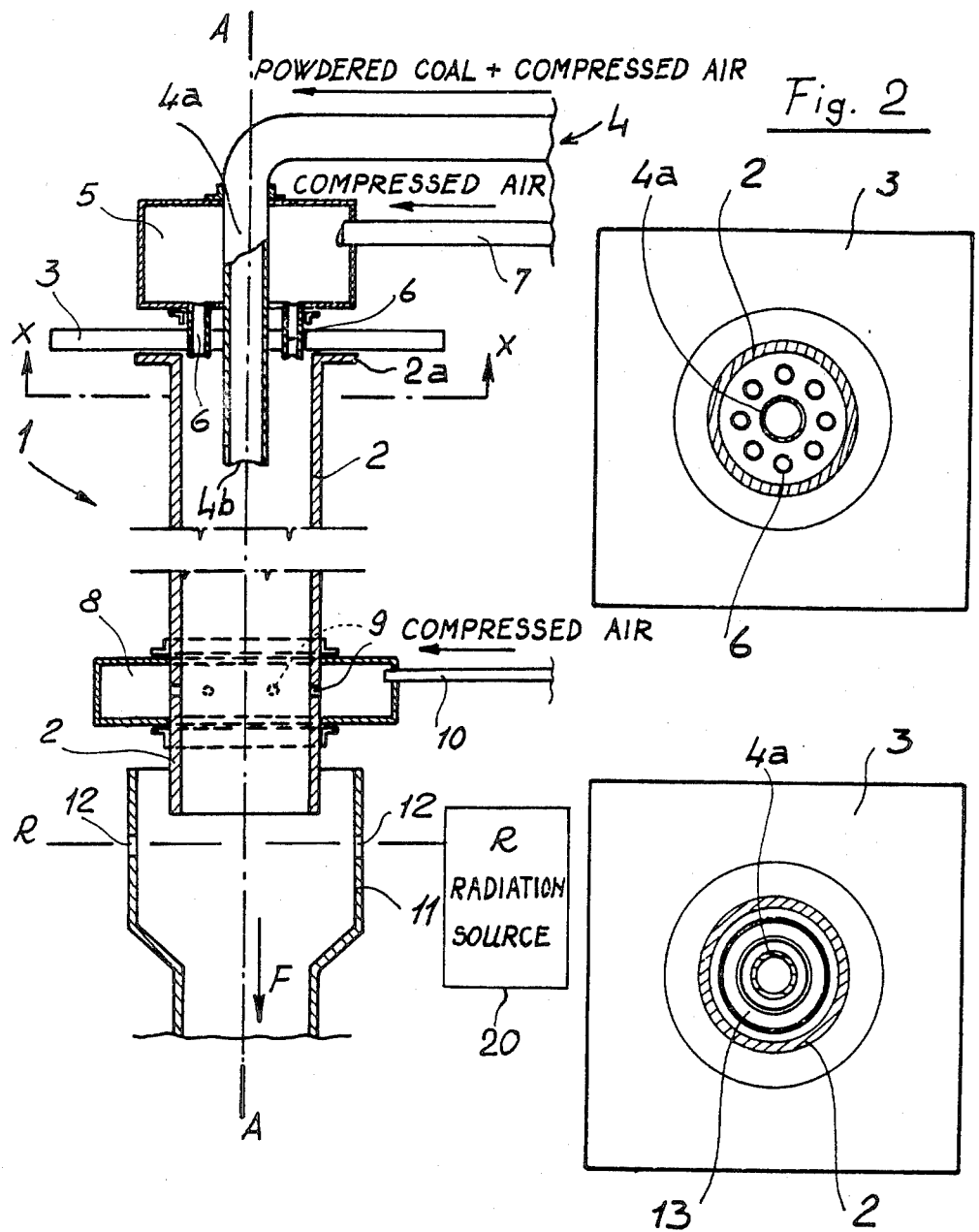

APPARATUS FOR MONITORING A STREAM OF COMMINUTED SOLID MATERIAL

BACKGROUND OF THE INVENTION

The present invention relates to testing or monitoring apparatus in general, and more particularly to improvements in apparatus for monitoring accumulations (particularly streams) of flowable comminuted solid material. For example, the apparatus of the present invention can be utilized with advantage for the monitoring of a stream of pulverulent coal or another mineral, of a stream of ground food products or the like.

Heretofore known apparatus for monitoring the flow of a comminuted solid material comprise a vessel, a device which admits the stream of comminuted material into the vessel, and a device which directs a beam of radiation (e.g., a beam of light or a laser beam) across the path of the stream in the vessel. An evaluation of the beam (called analyzing beam) which has traversed the stream of comminuted material in the vessel renders it possible to ascertain certain characteristics of the corresponding portion of the stream. The stream admitting device normally comprises a pipe which is coaxial with the vessel at the locus of entry and delivers comminuted solid material in a compressed gaseous carrier medium. The end portion of the pipe is bent at right angles close to the locus of entry into the vessel, and such conventional apparatus further comprise an injector which admits compressed air into the pipe at a location close to the bend in the pipe and is intended to impart to the solid material energy in order to cause such material to flow in the vessel in a manner which is suitable for analysis. As a rule, the injector is coaxial with the straight portion of the pipe which extends into the vessel.

The aforediscussed conventional monitoring apparatus exhibit the drawback that the comminuted material tends to adhere to the pipe as well as to the vessel. This exerts an adverse influence upon the homogeneousness of the material in the region where the material is traversed by the analyzing beam so that the analysis can furnish misleading results.

OBJECTS AND SUMMARY OF THE INVENTION

An object of the invention is to provide a novel and improved apparatus which can be utilized for the monitoring of a stream of cominuted solid material and which is constructed and assembled in such a way that the material entering the range of the analyzing beam or beams is more homogeneous than in heretofore known apparatus.

Another object of the invention is to provide an apparatus which is constructed and assembled in such a way that the conveyed material exhibits no tendency to adhere to the parts which come into contact therewith on the way toward the analyzing station.

A further object of the invention is to provide an apparatus wherein the condition of the comminuted material at the analyzing station can be influenced in several ways.

An additional object of the invention is to provide a novel and improved method of preparing a stream of comminuted solid material for analysis by one or more beams of visible light, by one or more laser beams or the like.

Still another object of the invention is to provide novel and improved means for regulating the flow of comminuted solid material on its way from the discharge end of a pneumatic conveyor toward the analyzing station.

The invention resides in the provision of an apparatus for monitoring a stream of comminuted solid material, particularly a stream of pulverulent material. The apparatus comprises an elongated vessel having a first end and a second end, a pneumatic conveyor including a conduit which serves to deliver a stream of cominuted material in a compressed gaseous carrier medium and has an end portion extending through the first end and into the interior of the vessel so that the discharge end of the end portion of the conduit is spaced apart from the first end of the vessel, means for propelling the admitted comminuted material longitudinally of and toward the second end of the vessel including means for discharging into the vessel at least one first current of a compressed gaseous fluid from a location between the first end of the vessel and the discharge end of the end portion of the conduit and toward the second end of the vessel, means for admitting into the vessel at least one second current of compressed gaseous fluid substantially radially inwardly and at a location between the discharge end of the end portion of the conduit and the second end of the vessel, and a source of radiation which serves to direct at least one beam of radiation transversely of the flow of comminuted material downstream of the admitting means, as considered in the direction of flow of comminuted material. The vessel can include an upright hollow cylinder and the end portion of the conduit is preferably coaxial with and extends downwardly through the upper end of such cylinder. The admitting means can comprise means for introducing into the cylinder several second currents substantially radially of the cylinder and at a level above the location where the flow of comminuted material is traversed by the beam of radiation.

The propelling means can include a plurality of nozzles which surround the end portion of the conduit in the cylinder and each of which serves to discharge a discrete first current of compressed gaseous fluid downwardly. Alternatively, the propelling means can comprise an annular nozzle which surrounds the end portion of the conduit in the interior of the cylinder and discharges a single first current of compressed gaseous fluids downwardy.

The propelling means can further comprise an annular chamber or another suitable source of compressed gaseous fluid which surrounds the conduit outwardly of the vessel, and the nozzle or nozzles of the propelling means receive compressed gaseous fluid from such source and extends or extend through the first end and into the interior of the vessel.

The admitting means can also comprise a source of gaseous fluid which preferably surrounds a portion of the vessel and the latter has one or more orifices for admission of one or more second currents from the respective source into the interior of the vessel.

The second end of the vessel is preferably open and the apparatus can further comprise a second vessel (e.g., a funnel-shaped container connected with an aspirator) which serves to receive comminuted material from the first named vessel by way of the open second end. The radiation source can be arranged to direct one or more beams of suitable radiation across the stream of comminuted material in the second vessel.

The gaseous carrier medium and/or the currents of compressed gaseous fluid may consist of or contain air.

The apparatus preferably further comprises support means for the first named vessel and the latter preferably extends substantially vertically downwardly from the support means. The support means preferably includes a portion which constitutes a cover for the first end of the first named vessel, and the nozzle or nozzles of the propelling means preferably extend through such cover to discharge one or more first currents of compressed gaseous fluid into the interior of the first named vessel at a level above the discharge end of the end portion of the conduit.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a somewhat schematic partly elevational and partly vertical sectional view of an apparatus which embodies the present invention;

FIG. 2 is a horizontal sectional view as seen in the direction of arrows from the line X—X of FIG. 1; and FIG. 3 is a sectional view similar to that of FIG. 2 but showing the nozzle of a modified propelling means.

DESCRIPTION OF THE PREFERRED EMBODIMENTS

Referring first to FIGS. 1 and 2, there is shown an apparatus 1 which is used to deliver a continuous stream of comminuted solid material (e.g., powdered coal) into the range of an analyzing beam R—R which is emitted by a suitable radiation source 20. The apparatus 1 comprises a first vessel 2 which is a vertical cylinder with a flange 2a at its upper end secured to a horizontal plate-like support 3 so that a portion of the support constitutes a closure or cover for the upper end of the vessel 2. The lower end of the vessel 2 is open and this vessel is coaxial with the end portion 4a of an elongated conduit 4 (e.g., a metallic pipe) which forms part of a pneumatic conveyor and serves to deliver into the vessel 2 a stream of comminuted solid material in a compressed gaseous carrier medium, e.g., air. The end portion 4a of the conduit 4 extends through a certain distance into the interior of the vessel 2 and the discharge end 4b of the end portion is disposed at a level below the support 3.

The means for propelling the particles of the stream of comminuted solid material downwardly and longitudinally of the vessel 2 to thereby reduce the likelihood of agglomeration of particles along the surfaces of the end portion 4a and vessel 2 comprises an annular chamber 5 which surrounds the conduit 4 at a level above the support 3 (i.e., externally of the vessel 2) and receives compressed air or another suitable gaseous fluid from a suitable source (not shown) by way of a pipe 7. The bottom wall of the chamber 5 carries an annulus of nozzles 6 (see FIG. 2) which extend downwardly through the support 3 and discharge first currents of compressed air into the vessel 2 at a level above the discharge end 4b. The nozzles 6 are preferably equidistant from each other, as considered in the circumferential direction of the end portion 4a, and their number can be increased above or reduced to less than eight. The axes of the nozzles 6 are preferably parallel to the axis of the preferably straight end portion 4a which is coaxial with the vessel 2. The axis of the vessel 2 is indicated by the phantom line A—A.

The apparatus further comprises means for admitting second currents of compressed gaseous fluid (preferably air) into the lower portion of the vessel 2 at a level below the discharge end 4b. Such admitting means comprises a ring-shaped chamber 8 which surrounds the vessel 2 close to the lower end of the latter and receives compressed gaseous fluid (preferably air) from a suitable source by way of a pipe 10. The vessel 2 has at least one annulus of orifices 9 which serve as a means for admitting second currents of gaseous fluid substantially radially of and into the vessel 2 at a level above the source 20 of radiation.

The open lower end of the vessel 2 extends with clearance into the open upper end portion of a substantially funnel-shaped second vessel 11 which is connected with an aspirator (not shown) serving to draw the particles of comminuted material in the direction which is indicated by the arrow F, i.e., across the path of the beam R—R. The vessel 11 has registering openings 2 for the passage of the beam R—R. The second vessel 11 can admit the tested material into a collecting receptacle, not shown.

The feature that the currents of compressed gaseous fluid which issue from the nozzles 6 enter the vessel 2 at a level above the discharge end 4b of the end portion 4a of the conduit 4 ensures that the material is prevented from adhering to the internal surface of the vessel 2 and is more likely to advance in the desired direction, namely first into the range of the currents issuing from the chamber 8 via orifices 9 and thereupon into the range of the beam R—R. The provision of means (including the chamber 8) for admitting into the vessel one or more second currents of gaseous fluid is desirable and advantageous because this ensures a more thorough intermixing of solid particulate material with air. It has been found that the improved apparatus greatly reduces the tendency of conveyed particulate material to settle on the conduit 4 and/or vessel 2 as well as that the homogeneousness of the stream of comminuted material which enters the range of the beam R—R is much more satisfactory for any selected interval of time than in heretofore known apparatus. This is achieved by the very simple and relatively inexpensive expedient of properly distributing and orienting the nozzles 6 and the orifices 9.

FIG. 3 shows a portion of a somewhat modified apparatus wherein the discrete nozzles 6 of the apparatus of FIGS. 1 and 2 are replaced with a single annular nozzle 13 spacedly surrounding the end portion 4a of the conduit and extending downwardly through that portion of the support 3 which constitutes a cover or closure for the upper end of the vessel 2. The latter is or can be identical with the first vessel of FIG. 1, i.e., it can constitute an upright cylinder whose axis coincides with the axis of the end portion 4a. If desired, the single circumferentially complete annular nozzle 13 of FIG. 3 can be replaced with two annular nozzles or it can be provided in addition to the nozzles 6 of FIG. 2. All that counts is to ensure that the first current or currents issuing from the nozzle or nozzles of the propelling means including the chamber 5 will cause the admitted comminuted solid material to advance at a predictable rate toward and into the range of the second current entering the vessel 2 via orifices 9 as well as that the current or currents issuing from the nozzle or nozzles of the propelling means will reduce the tendency of the conveyed solid material to adhere to the part 2 and/or 4a which could result in partial or complete clogging and hence in less predictable homogenizing of the material which is about to reach the analyzing station.

The conduits 7 and 10 can receive compressed air from a common main source or from two discrete main sources. Also, the conduit 4 can receive comminuted solid material from a single source or from two or more sources.

The vessels 2 and 11 can be said to constitute two components of a composite vessel wherein the beam R—R analyzes the decending material so that the device which processes the signals generated by the beam can ascertain, e.g., the dimensions of the granulae per lot.

The nozzle 13 or the nozzles 6 are used in lieu of conventional means for admitting propeller gas into the conduit of the pneumatic conveyor wherein the propeller gas causes turbulence and deposition of conveyed material on the conduit.

The stream of gaseous fluid which enters the vessel 2 via orifices 9 enhances the homogeneousness of the material which flows into the range of the beam R—R.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for monitoring a stream of comminuted solid material comprising an elongated first vessel having longitudinally spaced first and second ends, said second end being open; a pneumatic conveyor including a conduit arranged to deliver a stream of comminuted material, said conduit having an end portion which extends into the interior of said vessel through said first end and is provided with a discharge end between said first and second ends, and said end portion and said vessel cooperating to define a space in the region between said first and discharge ends; means for propelling the admitted material longitudinally of and toward the second end of said vessel, including means for discharging at least one first current of compressed gaseous fluid into said space in longitudinal direction of said vessel; means for admitting at least one second current of compressed gaseous fluid into said vessel substantially radially inwardly and at a location between said discharge end and said second end to form a mixture of comminuted material and gaseous fluid; a discrete second vessel arranged to receive the mixture of comminuted material and gaseous fluid by way of said open second end; and a source of radiation arranged to direct at least one beam of radiation across said second vessel and transversely of the flow of the mixture of gaseous fluid and comminutes material in said second vessel.

2. The apparatus of claim 1, wherein said first vessel includes an upright hollow cylinder and said first end is the upper end of said cylinder, said end portion of said conduit being coaxial with said cylinder and said admitting means including means for introducing into said cylinder several second currents substantially radially of said cylinder at a level above the beam of radiation issuing from said source.

3. The apparatus of claim 2, wherein said propelling means includes a plurality of nozzles surrounding the end portion of said conduit in said cylinder and each arranged to discharge a discrete first current of compressed gaseous fluid downwardly.

4. The apparatus of claim 2, wherein said propelling means comprises an annular nozzle surrounding the end portion of said conduit in the interior of said cylinder.

5. The apparatus of claim 1, wherein said propelling means comprises a source of compressed gaseous fluid surrounding said conduit outwardly of said first vessel and at least one nozzle receiving gaseous fluid from the respective source and extending through the first end and into the interior of said first vessel.

6. The apparatus of claim 1, wherein said admitting means comprises a source of compressed gaseous fluid surrounding a portion of said first vessel, said first vessel having at least one orifice for admission of the second current from the respective source into said vessel.

7. The apparatus of claim 1, wherein said discharge end is located substantially centrally of said first vessel and said gaseous carrier medium as well as said gaseous fluid is air.

8. The apparatus of claim 1 further comprising support means for said first vessel, said first vessel extending downwardly from said support means and the latter including a closure for the first end of said first vessel, said propelling means including at least one substantially vertical nozzle extending through said closure and into the upper part of said vessel.

9. The apparatus of claim 1, wherein said conduit is arranged to deliver a stream of comminuted material in a compressed gaseous carrier medium.

10. The apparatus of claim 1, wherein said space is substantially annular and said discharging means is arranged to discharge an annulus of discrete first currents into said space.

11. The apparatus of claim 1, wherein said space is substantially annular and said discharging means is arranged to discharge a substantially annular first current into said space.

* * * * *